US009827365B2

(12) United States Patent
Min et al.

(10) Patent No.: US 9,827,365 B2
(45) Date of Patent: Nov. 28, 2017

(54) SYSTEMS AND METHODS FOR AUTOMATED AIR REMOVAL IN PRODUCTS COMPRISING BIOLOGICAL FLUIDS (71) Applicant: Fenwal, Inc., Lake Zurich, IL (US)

(72) Inventors: Kyungyoon Min, Kildeer, IL (US); Katherine N. Radwanski, Highland Park, IL (US); Tanima Jahan Abedin, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/259,176

(22) Filed: Sep. 8, 2016

(65) Prior Publication Data
US 2017/0119949 A1 May 4, 2017

Related U.S. Application Data (60) Provisional application No. 62/249,462, filed on Nov. 2, 2015.

(51) Int. Cl.
*B01D 46/46* (2006.01)
*B01D 53/30* (2006.01)
(Continued)

(52) U.S. Cl.
CPC ........ *A61M 1/3627* (2013.01); *A61M 1/0259* (2013.01); *A61M 1/3496* (2013.01);
(Continued)

(58) Field of Classification Search
None
See application file for complete search history.

(56) References Cited

U.S. PATENT DOCUMENTS 5,217,627 A     6/1993  Pall et al.
2002/0131891 A1*  9/2002  Smith ................. A61M 1/0209
                                                422/44
(Continued)

FOREIGN PATENT DOCUMENTS

WO    WO93/25295 A1    12/1993
WO    WO03/033046 A2    4/2003

OTHER PUBLICATIONS

European Patent Office, European Search Report, counterpart EP Appl. No. 16193358, dated Mar. 21, 2017.

*Primary Examiner* — Amber R Orlando
*Assistant Examiner* — Phillip Y Shao
(74) *Attorney, Agent, or Firm* — Cook Alex Ltd.

(57) ABSTRACT

Methods and systems are provided automatically removing air from a collection container for a blood product. The system comprises a disposable flow circuit including a tubing in fluid communication with the collection container and a durable hardware component. A programmable controller operates the pump in a first/forward direction to flow the target product into the collection container; determines that substantially all the target product has been pumped into the collection container; and operates the pump in the first/forward direction to pump a chase volume of air into the collection container along with any target product remaining in the tubing. In one embodiment, after the chase volume of air is pumped into the collection container, the controller operates the pump in a second/reverse direction for removing air from the collection container, and stops operation of the pump when the amount of air removed from the collection container is substantially equal to the residual volume of air.

13 Claims, 6 Drawing Sheets

(51) Int. Cl.
  *A61M 1/36* (2006.01)
  *A61M 1/02* (2006.01)
  *A61M 1/38* (2006.01)
  *A61M 1/34* (2006.01)
  *B01D 19/00* (2006.01)
  *A61J 1/10* (2006.01)

(52) U.S. Cl.
  CPC ............ *A61M 1/3693* (2013.01); *A61M 1/38* (2013.01); *B01D 19/0031* (2013.01); *B01D 19/0052* (2013.01); *A61J 1/10* (2013.01)

(56) References Cited

U.S. PATENT DOCUMENTS

| | | | |
|---|---|---|---|
| 2003/0199803 A1* | 10/2003 | Robinson | A61M 1/3693 604/6.04 |
| 2009/0211962 A1 | 8/2009 | Min et al. | |
| 2009/0211989 A1* | 8/2009 | Nguyen | A61K 35/16 210/767 |
| 2011/0192745 A1* | 8/2011 | Min | A61M 1/0209 206/370 |
| 2012/0291867 A1 | 11/2012 | Gassman et al. | |

\* cited by examiner

*MAY OCCUR BEFORE OR AFTER RESIDUAL AIR IS REMOVED

SYSTEMS AND METHODS FOR AUTOMATED AIR REMOVAL IN PRODUCTS COMPRISING BIOLOGICAL FLUIDS

FIELD OF THE DISCLOSURE

The present disclosure is directed to systems and methods for performing an procedures involving the separation of biological fluids and, more particularly, to systems and methods for the automated removal of residual air from a container of a biological fluid, such as a cell product or plasma collected in an apheresis procedure.

When blood is being collected or separated, e.g., in an apheresis procedure, into its various components, (such as red blood cells, plasma, platelet-rich plasma, white blood cells), some amount of air invariably is forced into the collection container for the blood or its separated constituents. As is well known, exposure of blood and blood products to air can result in a degradation of the blood/blood product due to, e.g., clotting, coagulation, etc., as well as create an environment conducive to bacterial growth. Additionally, residual air in the blood product may also adversely affect any subsequent processing of the blood product (such as, e.g., pathogen inactivation, photopheresis, etc.). Consequently, when blood/blood product is being stored in a container for later treatment extracorporeal or for reinfusion to the donor or patient, it is important to minimize, and preferably eliminate, any interface within the storage container between the air and the blood/blood product contained therein.

The removal of air from a collection container may be performed manually in a procedure called "burping." For example, if a flexible collection container is used, the air in the collection container is burped by squeezing the collection container to force the air contained therein back into the disposable collection kit. Alternatively, the container may include a length of tubing leading to an "air burp bag." The air is removed from the collection container by closing the inlet to the container (e.g., with a clamp), and the collection container is squeezed to force air into the air burp bag. In either method, when blood/blood product starts to enter the tubing after all the air is evacuated, the collection container will be closed or sealed.

Manual burping of the collection container can result in variability in terms of the completeness of the removal of the residual air from the container, and also runs the risk of losing a portion of the blood/blood product if burping is continued beyond the point of air removal. Consequently, automated burping of the collection container has also been proposed in connection with blood collection and separation devices that include a pump for flowing the blood/blood product into the collection container. For example, in US 2009/0211962, incorporated herein by reference, an automated burping process is disclosed by which a pump is first operated in a forward direction to pump fluid through a conduit or tubing into the collection container, and then operated in a reverse direction to remove the air from the container. An optical sensor is associated with the tubing to detect the interface between fluid and air in the tubing such that when an air-fluid interface is detected, the pump receives a signal to stop operating in the reverse direction.

By way of the present application, an improved automated air removal system and method are disclosed that maximize the amount of blood/blood product flowed through the conduit/tubing into the collection container by minimizing the amount retained in the conduit/tubing.

SUMMARY OF THE DISCLOSURE

In accordance with the disclosure, a method for automatically controlling a system for separating biological fluids (such as an apheresis system for the separation of blood) to remove air from a collection container into which a target product (such as a cellular or plasma product) has been flowed is provided in which the system comprises a disposable flow circuit including a tubing in fluid communication with the collection container and a durable hardware component including a pump for engaging the tubing to flow fluid therethrough that includes a programmable controller for operating the pump.

In one aspect, the method comprises the programmable controller operating the pump in a first/forward direction to flow the target product into the collection container; determining that substantially all the target product has been pumped into the collection container; and operating the pump in the first/forward direction to pump a chase volume of air into the collection container along with any target product remaining in the tubing.

In another aspect, after the chase volume of air is pumped into the collection container, such that a residual volume of air is contained in the collection container, the method further comprises the programmable controller operating the pump in a second/reverse direction for removing air from the collection container; stopping operation of the pump when the amount of air removed from the collection container is substantially equal to the residual volume of air; and sealing the collection container.

In a further aspect, the residual volume of air comprises the chase volume plus an initial volume of air contained in the collection container after substantially all the target product has been pumped into the collection container but before pumping the chase volume of air into the collection container.

The initial volume of air contained in the collection container may be determined empirically. Alternatively, the chase volume of air may be determined empirically and a value for the residual volume of air pre-programmed into the controller. In the latter case, the chase volume of air is calculated based on an internal diameter of the tubing and number of pump cycles required to pump the chase volume into the collection container; a value for the initial volume of air in the collection container is pre-programmed into the controller; the controller calculates a value for the total volume of residual air; and the pump is operated in the second, reverse direction a sufficient number of cycles to remove the residual volume of air from the collection container.

In a another aspect, the hardware component further comprises a sensor for detecting an air-fluid interface in the tubing, and the method further comprises the programmable controller operating the pump in the first, forward direction to pump the chase volume of air into the collection container upon a first sensing of the air-fluid interface until the residual volume of air is contained in the collection container, operating the pump in the second, reverse direction to remove air from the container, and stopping operation of the pump in the second, reverse direction after the residual volume of air has been removed from the collection container by operation of the pump. Optionally, the operation of the pump in the second, reverse direction may be stopped upon a second sensing of the air fluid interface.

The collection container may comprise a flexible container having a single top port through which the target product is flowed into the collection container. Alternatively, the flexible container may have a top port and a bottom port, with the target product being flowed into the collection container through the bottom port and the residual air is pumped out of the collection container and back into the fluid circuit through the top port.

In another aspect, the collection container may comprise a rigid container with a top port having a flexible container in flow communication therewith and a bottom port. The target product is flowed into the collection container through the bottom port until the collection container is filled, and the determination that substantially all the target product has been pumped into the collection container is based on a calculated volume of fluid moved through the tubing by operation of the pump, such that the air in the rigid container is displaced into the flexible container.

According to the present disclosure, a system is also provided for automatically removing air from a collection container into which a cellular or plasma target product has been flowed. The system comprises a disposable flow circuit including a tubing in fluid communication with the collection container and a durable hardware component including a pump for engaging the tubing to flow fluid therethrough and a programmable controller for operating the pump. The programmable controller is configured to operate the pump in a first/forward direction to flow the target product into the collection container; determine that substantially all the target product has been pumped into the collection container; and operate the pump in the first/forward direction to pump a chase volume of air into the collection container along with any target product remaining in the tubing.

In another aspect, the controller may be configured so that, after the chase volume of air is pumped into the collection container, so that a residual volume of air comprising the chase volume and the initial volume is contained in the collection container, the controller operates the pump in a second/reverse direction for removing air from the collection container; and stops operation of the pump when the amount of air removed from the collection container is substantially equal to the residual volume of air.

Other aspects of the disclosure will become apparent upon references to the accompanying figures and following detailed description.

DESCRIPTION OF THE ILLUSTRATED EMBODIMENTS

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

In accordance with the present disclosure, residual air in a collection container for a biological fluid, such as plasma or cell product collected in a blood separation procedure, is removed in an automated fashion during the procedure. The procedure may be an apheresis procedure, where a replacement fluid is returned to a donor/patient, such as a donor apheresis procedure (e.g. platelet, plasma or erythrocytepheresis collections) or a therapeutic apheresis procedure (e.g. MNC collection, photopheresis). The procedure may also be a single-pass blood separation procedure, where no replacement fluid is returned to the donor, or a post-collection separation or washing procedure for previously-collected blood or blood product. The purpose of air removal is to aid in cell product storage or subsequent treatment/processing steps, and may be applicable with respect to other procedures for the separation of biological fluids utilizing a pump controlled by a programmable controller.

The system and method are applicable to procedures that use either a flexible collection container or a rigid collection container. When a flexible container is utilized, and the container has a top port through which the target product is introduced into the container, the system and method provide for "chasing" with an extra volume of air pumped from disposable kit into collection container in order to push all of the target product remaining in the kit into collection container. All of the air that is in the collection container is then pumped back into disposable kit. If a flexible collection container having both a top and a bottom port is used, the target product is transferred into the collection container through the bottom port, and the residual air is pumped back into disposable set through the top port.

The pump may be operated a sufficient number of cycles to remove a calculated volume of air from the container, the calculated volume being equal to the "chase" volume of air pumped plus an initial volume of air in the collection container before pumping of the chase volume. The value for the initial volume of air originally in collection container may be determined empirically, and pre-programmed into the controller. The chase volume of air may also be determined empirically and pre-programmed into the controller.

Alternatively, the chase volume of air may be calculated based on an internal diameter of the tubing and number of pump cycles required to pump the chase volume into the collection container. As a further alternative, instead of using empirically-determined and/or calculated volumes for the residual air in the container after the chase air is pumped, an optical sensor may be associated with the tubing that detects an air/fluid interface and generates a signal to stop operation of the pump when the air/fluid interface is detected.

The system and method may also be used with a rigid collection container having a bottom port, through which the target product is flowed into the collection container, and a top port having a small volume flexible bag connected thereto by a length of tubing. The target product is flowed into the collection container through the bottom port until the collection container is filled. The determination that substantially all the target product has been pumped into the collection container may be based on a calculated volume of fluid moved through the tubing by operation of the pump. The air that was in the rigid container will be displaced into the flexible container connected to the top of the collection container.

Figure 1:
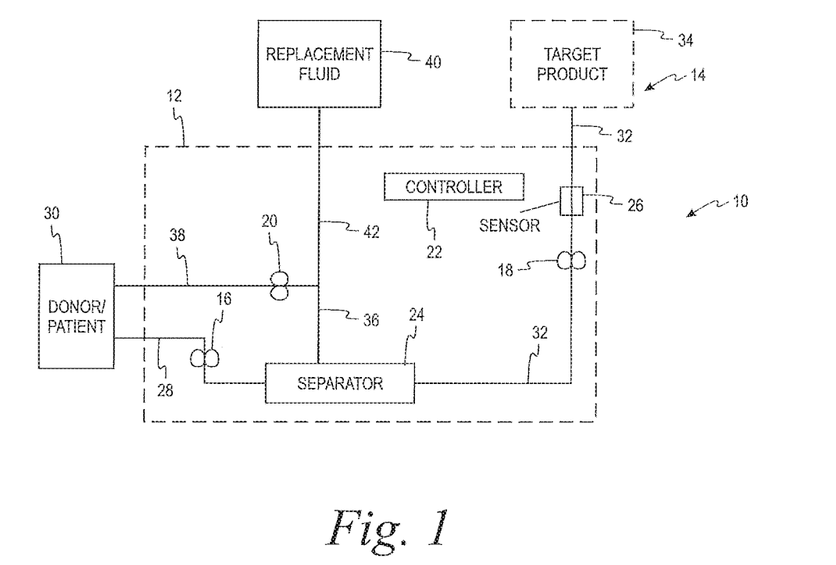
FIG. 1 is a schematic diagram of a system for performing automated removal of air from a collection container in accordance with the present disclosure.

Turning to FIG. 1, there is seen a schematic and simplified representation of a blood processing system 10 embodying the systems and capable of utilizing the methods of the present disclosure. The system 10 includes a durable hardware component 12 and a single-use disposable flow circuit 14. The durable hardware component comprises a series of pumps 16, 18 and 20, for moving fluid through the various flow paths of the flow circuit 14. While three pumps are shown, hardware configurations with fewer or more pumps may be utilized, depending on the kit configuration and the procedure being performed. The pumps are controlled by means of a programmable controller 22. In FIG. 1, the hardware component 12 also includes a separator 24, and a sensor 26 for detecting the presence or absence of fluid in an associated tubing, and generating a signal indicative of the same.

The separator 24 may be a centrifugal separator, such as that shown in, e.g., U.S. Pat. No. 5,868,696, or a spinning membrane separator, such as that shown in, e.g., U.S. Pat. No. 5,194,145. If the separator 24 is of the centrifugal type, the disposable flow circuit 14 typically includes a separation chamber that is received in the centrifuge. If the separator 24 is of the spinning membrane type, it more typically forms an integral component of the disposable flow circuit 14, rather than part of the hardware component. It should be noted that the type of separator used, and whether it is part of the hardware component or the disposable flow circuit, are not factors in the applicability of the systems and methods of the present application.

The disposable flow circuit 14 comprises a series of interconnected tubings and containers. Specifically, the flow circuit comprises a first flow path 28 between a source 30 of biological fluid to be processed and the separator 24. The source 30 of biological fluid may be a donor/patient, or a container of previously-collected biological fluid, without departing from the disclosure. As illustrated, the flow path 28 is acted on by pump 16 to flow biological fluid from the source 30 to the inlet of separator 24.

A second flow path 32 is provided for flowing the target product from the separator 24 to a collection container 34. The second flow path 32 is acted on by pump 18 to flow the target product from a first outlet of the separator into the collection container 34. The tubing comprising flow path 32 is also associated with the sensor 26 that detects the fluid/air interface in the flow path. The sensor preferably is associated with the flow path 32 at a location intermediate of the pump 18 and the collection container 34.

The fluid circuit comprises a tubing forming third flow path 36 through which the non-targeted components of the biological fluid are flowed from a second outlet of the separator 24. If the source 30 of the biological fluid is a container of previously collected fluid, the non-targeted components may be flowed through the flow path 36 into a second container, and disposed of accordingly. In the illustrated embodiment, the source 30 of the biological fluid is a donor/patient, and the non-targeted components are returned to the donor/patient through a fourth flow path 38 that is in fluid communication with flow path 36. As illustrated, the tubing comprising flow path 38 is acted on by pump 20 to return the non-targeted components to the donor/patient at a controllable rate.

Additionally, the procedure being performed may require that a replacement fluid may be returned to the donor/patient. As such, in the illustrated embodiment, the flow circuit 14 includes a container 40 of replacement fluid that is connected by a tubing forming a fifth flow path 42 between the container 40 and the flow path 38.

Figure 2A:
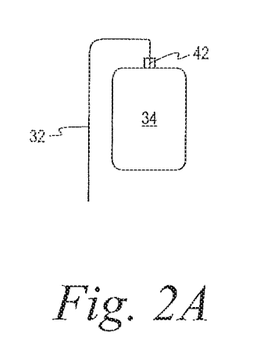
FIGS. 2A, 2B and 2C are schematic diagrams of three different collection containers that may be used in the disclosed automated air removal systems and methods.
Figure 2B:
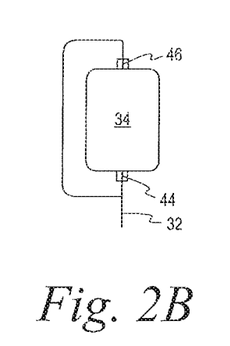

As discussed above, the target product collection container 34 may take different forms, without departing from the disclosure. With reference to FIGS. 2A and 2B, the collection container 34 is a flexible container or bag. In FIG. 2A, the container 34 has a single top port 42 through which target product (and air) may be flowed through flow path 32 to and from the container 34. In FIG. 2B, the container has a bottom port 44 through which target product (and air) is flowed into the container 34 and a top port 46 through which air is evacuated from the container 32 and returned into the flow circuit.

Figure 2C:
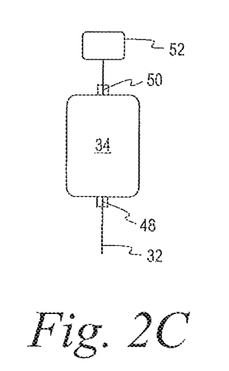

With reference to FIG. 2C, the target product container 34 comprises a rigid container having a single bottom port 48 through which target product (and air) may be flowed through the flow path 32 into the container 34 and a top port 50 through which air displaced by the target product is flowed into a flexible container 52.

Figure 3:
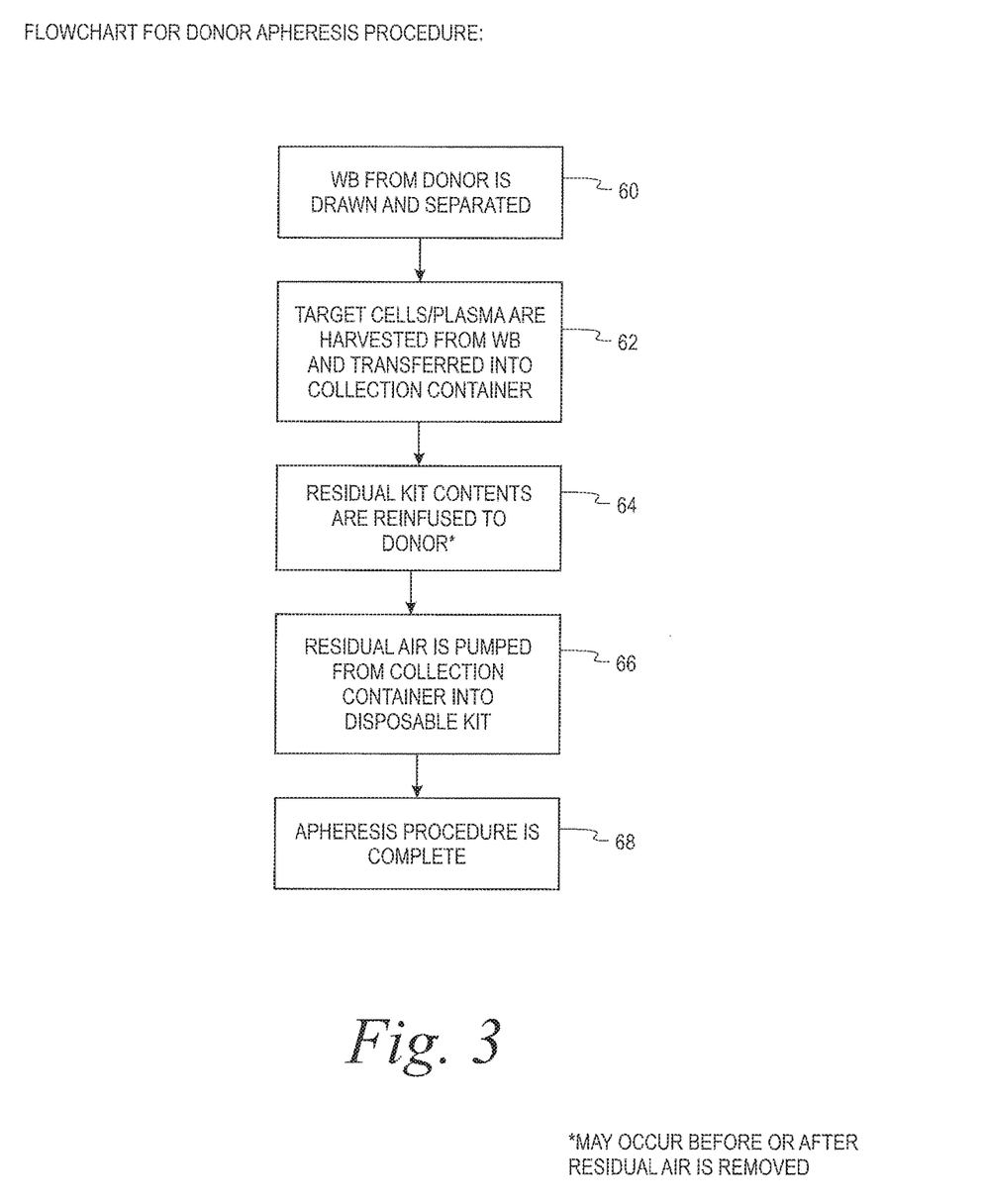
FIG. 3 is a flowchart setting forth the steps for a donor apheresis procedure performed in accordance with the present disclosure using a flexible collection container.
Figure 4:
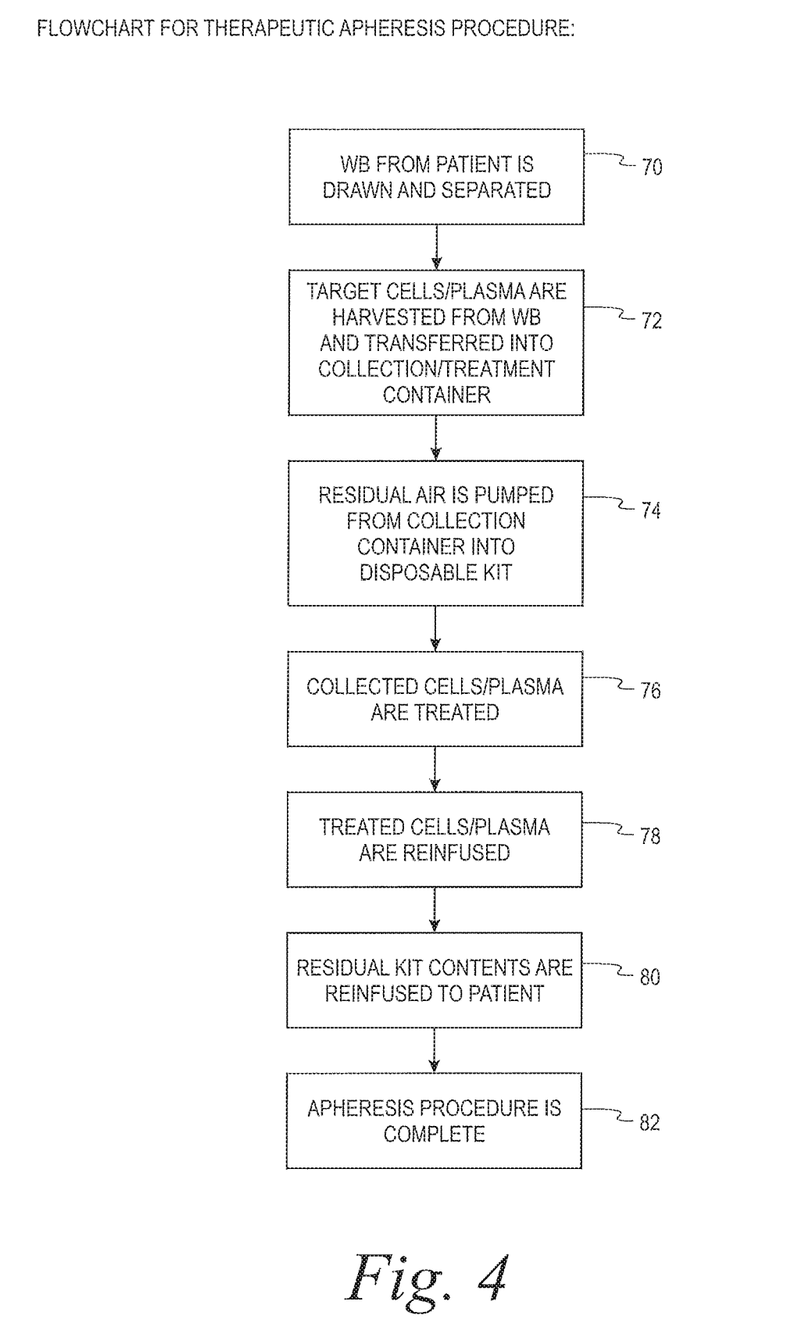
FIG. 4 is a flowchart setting forth the steps for a therapeutic apheresis procedure performed in accordance with the present disclosure using a flexible collection container.
Figure 5:
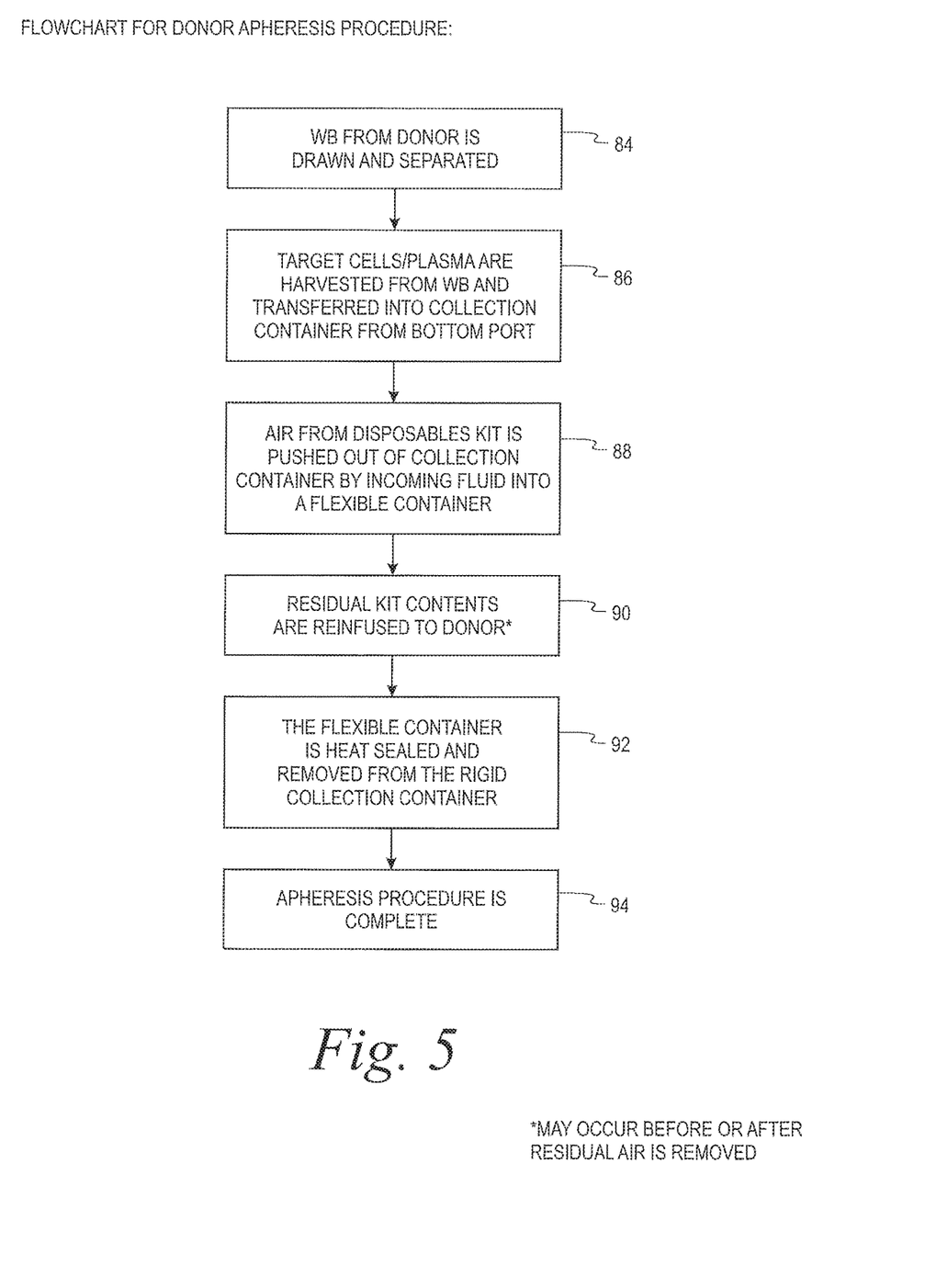
FIG. 5 is a flowchart setting forth the steps for a donor apheresis procedure performed in accordance with the present disclosure using a rigid collection container.
Figure 6:
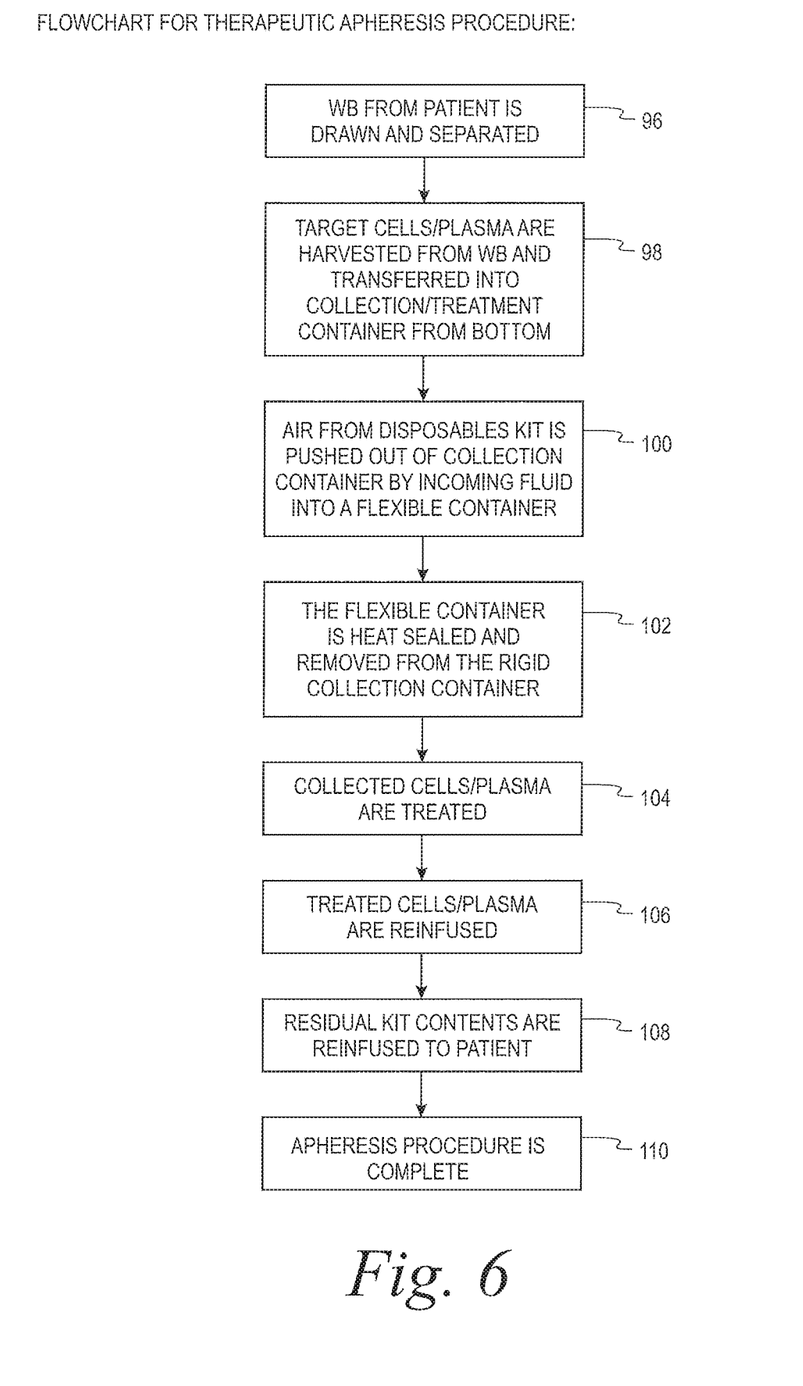
FIG. 6 is a flowchart setting forth the steps for a therapeutic apheresis procedure in accordance with the present disclosure using a rigid container.

The automated air removal systems and methods described above may be advantageously used in connection with any number of different blood processing procedures. With reference to FIGS. 3-6, flow charts for representative procedures are shown, such procedures being for the purposes of illustration and not by way of limitation. The flow charts of FIGS. 3 and 4 are directed to procedures in which a flexible collection container is used, while FIGS. 5 and 6 are directed to procedures in which a rigid collection container is used.

Turning to FIG. 3, a flow chart is seen for a donor apheresis procedure using a flexible collection container, such as that illustrated in FIGS. 2A and 2B. In a first step 60, whole blood is withdrawn from a donor and is separated to produce a target product and a non-target product. The target product may be one or more of a particular cell type and or plasma, with the non-target product being the remainder.

In step 62, the target product (either cellular or plasma) is transferred to the collection container. This is done by operation of a pump, such as pump 18 in FIG. 1. In step 64, the residual kit contents, which may comprise the non-target products plus any additional replacement fluid, are reinfused to the donor. In the system of FIG. 1, the reinfusion is performed by operation of the pump 20. After the reinfusion of the residual kit contents, the access line (flow path 28 in FIG. 1) may be removed from the donor.

In step 66, the residual air is pumped from the collection container back into the kit. As noted above, this residual air includes the chase volume of air used to clear the kit tubing of any remaining target product (i.e. the tubing forming flow path 32 in FIG. 2). The residual air is pumped back into the kit by operating the pump 20 in the reverse direction until all the residual air is removed from the collection container, as determined in accordance with the methods described above.

The apheresis procedure is then complete, as indicated in step 68, upon which the collection container may be sealed and the remainder of the flow circuit otherwise disposed of. Note that step 64, the reinfusion of the residual kit contents into the donor, may be performed before or after step 66.

The flowchart of FIG. 4 is directed to a therapeutic apheresis procedure using a flexible collection container, such as that illustrated in FIGS. 2A and 2B. In a typical therapeutic apheresis procedure, whole blood is withdrawn from a patient and the target product is separated out and then treated before being reinfused into the patient. The collection container for the target product is also the container within which the subsequent treatment of the target product occurs. The therapeutic apheresis procedure of FIG. 4 includes steps 70-82, some of which correspond to the steps of the procedure of FIG. 3. Specifically, step 70 of FIG. 4 corresponds to step 60 of FIG. 3, step 72 corresponds to step 62, step 74 corresponds to step 66, step 80 corresponds to step 64, and step 82 corresponds to step 68. As such, these steps of the therapeutic apheresis procedure will not be discussed in greater detail.

In the therapeutic apheresis procedure, after the residual air is removed from the collection container/treatment container, the contents of the container are treated to provide for the desired therapeutic effect, as set forth in step 76. The treated target product is then reinfused into the patient, in accordance with step 78.

Turning to FIG. 5, the steps for performing a donor apheresis procedure with a rigid container, such as that illustrated in FIG. 2C, is shown. In a first step 84, whole blood is withdrawn from a donor and is separated to produce a target product and a non-target product. The target product may be one or more of a particular cell type and or plasma, with the non-target product being the remainder.

In step 86, the target product (either cellular or plasma) is transferred to the rigid collection container through the bottom port 48. This is done by operation of a pump, such as pump 18 in FIG. 1. In step 88, the residual air in the collection container, including the air from the flow circuit and the chase volume of air, is displaced from the collection container out through the top port 50 and into the flexible container 52. In step 90, the residual kit contents, which may comprise the non-target products plus any additional replacement fluid, are reinfused to the donor by operation of the pump 20. After the reinfusion of the residual kit contents, the access line (flow path 28 in FIG. 1) may be removed from the donor.

In step 92, the flexible container 52 containing the residual air displaced form the collection container is sealed (by, e.g., heat sealing) and detached or otherwise removed from the collection container.

The apheresis procedure is then complete, as indicated in step 94, upon which the collection container may be sealed and the remainder of the flow circuit otherwise disposed of. Note that step 90, the reinfusion of the residual kit contents into the donor, may be performed before or after step 88.

The flowchart of FIG. 6 is directed to a therapeutic apheresis procedure using a rigid collection container, such as that illustrated in FIG. 2C. The therapeutic apheresis procedure of FIG. 6 includes steps 96-110, some of which correspond to the steps of the procedure of FIG. 5. Specifically, step 96 of FIG. 6 corresponds to step 84 of FIG. 4, step 98 corresponds to step 86, step 100 corresponds to step 88, step 102 corresponds to step 92, step 106 corresponds to step 90, and step 110 corresponds to step 94. As such, these steps of the therapeutic apheresis procedure using a rigid collection container will not be discussed in greater detail.

In the therapeutic apheresis procedure, after the container 52 for the residual air is removed from the collection container/treatment container, the contents of the container are treated to provide for the desired therapeutic effect, as set forth in step 104. The treated target product is then reinfused into the patient, in accordance with step 1.

Thus, an improved method and system for the automatic removal of air from a collection container for biological fluid has been disclosed. The description provided above is intended for illustrative purposes, and is not intended to limit the scope of the disclosure to any particular method, system, apparatus or device described herein.

The invention claimed is:

1. A method for automatically controlling a system for separating biological fluids to remove air from a collection container into which a target product has been flowed, the system comprising a disposable flow circuit including a tubing in fluid communication with the collection container and a durable hardware component including a pump for engaging the tubing to flow fluid therethrough and a programmable controller for operating the pump, the method comprising:
   a) the programmable controller operating the pump in a first, forward direction to flow the target product into the collection container;
   b) the programmable controller determining that substantially all the target has been pumped into the collection container;
   c) the programmable controller operating the pump in the first, forward direction to pump a chase volume of air into the collection container along with any target product remaining in the tubing so that a residual volume of air is contained in the collection container comprising an initial volume of air after substantially all the target product has been pumped into the collection container but before pumping the chase volume of air into the collection container plus the chase volume;
   d) the programmable controller operating the pump in a second, reverse direction for removing air from the collection container; and
   e) the programmable controller stopping operation of the pump when the amount of air removed from the collection container is substantially equal to the residual volume of air;
      wherein the initial volume of air is determined empirically and the chase volume of air is calculated based on an internal diameter of the tubing and number of pump cycles required to pump the chase volume into the collection container; a value for the initial volume of air in the collection container is pre-programmed into the controller; the controller calculates a value for the total volume of residual air; and the pump is operated in the second, reverse direction a sufficient number of cycles to remove the residual volume of air from the collection container.

2. The method of claim 1 wherein the hardware component further comprises a sensor for detecting an air-fluid interface in the tubing, the method further comprising the programmable controller operating the pump in the first, forward direction to pump the chase volume of air into the collection container upon a first sensing of the air-fluid interface until the residual volume of air is contained in the container, operating the pump in the second, reverse direction to remove air from the container, and stopping operation of the pump in the second, reverse direction after the residual volume of air has been removed from the collection container by operation of the pump.

3. The method of claim 2 wherein the operation of the pump in the second, reverse direction is stopped upon a second sensing of the air-fluid interface.

4. The method of claim 1 wherein the residual air is pumped from the collection container back into the flow circuit.

5. The method of claim 1 wherein the collection container comprises a flexible container having a single top port.

6. The method of claim 1 wherein the collection container comprises a flexible container with a top port and a bottom port, the target product is flowed into the collection container through the bottom port, and the residual air is pumped out of the collection container back into the fluid circuit through the top port.

7. The method of claim 1 wherein the collection container comprises a rigid container with a top port having a flexible container in flow communication therewith and a bottom port, the target product is flowed into the collection container through the bottom port until the collection container is filled, and the determination that substantially all the target product has been pumped into the collection container is based on calculated volume of fluid moved through the tubing by operation of the pump, air in the rigid container being displaced into the flexible container.

8. The method of claim 1 wherein the collection container is sealed by permanent seal.

9. The method of claim 1 wherein the collection container is sealed by application of a clamp to the tubing.

10. A system for automatically removing air from a collection container into which a target product has been flowed, the system comprising:
   a) a disposable flow circuit including a tubing in fluid communication with the collection container;
   b) a durable hardware component including a pump for engaging the tubing to flow fluid therethrough and a programmable controller for operating the pump, the programmable controller being configured to operate the pump in a first/forward direction to flow the target product into the collection container; determine that substantially all the target product has been pumped into the collection container; and operate the pump in the first/forward direction to pump a chase volume of air into the collection container along with any target product remaining in the tubing; and
   c) wherein the controller is further configured so that, after the chase volume of air s pumped into the collection container, with a residual volume of air being contained in the collection container, the controller operates the pump in a second/reverse direction for removing air from the collection container; and stops operation of the pump when the amount of air removed from the collection container is substantially equal to the residual volume of air, wherein the residual volume of air comprises the chase volume plus an initial volume of air contained within the collection container after substantially all the target product has been pumped into the collection container but before pumping the chase volume of air into the collection container, wherein the initial volume of air is determined empirically, and wherein the chase volume of air is calculated based on an internal diameter of the tubing and number of pump cycles required to pump the chase volume into the collection container; a value for the initial volume of air in the collection container is pre-programmed into the controller; the controller calculates a value for the total volume of residual air; and the pump is operated in the second, reverse direction a sufficient number of cycles to remove the residual volume of air from the collection container.

11. The system of claim 10 wherein the collection container comprises a flexible container having a single top port.

12. The system of claim 10 wherein the collection container comprises a top port and a bottom port, so that the target product is flowed into the collection container through the bottom port and the residual air is pumped out of the collection container and back into the fluid circuit through the top port.

13. The system of claim 10 wherein the collection container may comprise a rigid container with a top port having a flexible container in flow communication therewith and a bottom port so that the target product is flowed into the collection container through the bottom port and the air in the rigid container is displaced into the flexible container.

* * * * *